(12) United States Patent
Holm et al.

(10) Patent No.: US 10,112,030 B2
(45) Date of Patent: Oct. 30, 2018

(54) INTRODUCER SHEATH ASSEMBLY HAVING A LOCKING DILATOR

(71) Applicant: W. L. Gore & Associates, Inc., Newark, DE (US)

(72) Inventors: Brian C. Holm, Mountain View, CA (US); Shane P. Rogers, San Jose, CA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/384,699

(22) Filed: Dec. 20, 2016

(65) Prior Publication Data

US 2017/0100566 A1 Apr. 13, 2017

Related U.S. Application Data

(62) Division of application No. 13/677,839, filed on Nov. 15, 2012, now Pat. No. 9,561,347.

(Continued)

(51) Int. Cl.
*A61M 25/01* (2006.01)
*A61B 17/34* (2006.01)
*A61M 25/00* (2006.01)
*A61M 25/06* (2006.01)
*A61M 29/00* (2006.01)
(Continued)

(52) U.S. Cl.
CPC ..... *A61M 25/0105* (2013.01); *A61B 17/3421* (2013.01); *A61M 25/0009* (2013.01); *A61M 25/0097* (2013.01); *A61M 25/0662* (2013.01); *A61M 29/00* (2013.01); *A61M 39/22* (2013.01);
(Continued)

(58) Field of Classification Search
CPC .......... A61M 25/0105; A61M 25/0662; A61M 25/0097; A61M 2025/0006; A61M 29/00; A61B 17/3421; A61B 2017/347; A61B 2017/00477
See application file for complete search history.

(56) References Cited

U.S. PATENT DOCUMENTS 4,610,242 A 9/1986 Santangelo
5,158,553 A * 10/1992 Berry ................. A61B 17/3462
604/167.03
(Continued)

FOREIGN PATENT DOCUMENTS

DE 19724282 C1 10/1998
JP 1995178179 A 7/1995
(Continued)

OTHER PUBLICATIONS

International Search Report and Written Opinion for PCT/US2012/065536 dated Feb. 18, 2013, corresponding to U.S. Appl. No. 13/677,839, 9 pages.
(Continued)

*Primary Examiner* — Amber Stiles

(57) ABSTRACT

An introducer assembly includes a valve having a first end and an opposite second end; a sheath fixedly secured to and extending axially from one of the first and second ends of the valve; a dilator extending through the valve and sheath; and a lock knob rotatable between locked and unlocked positions to releasably axially lock the tool relative to the sheath without causing corresponding rotation of the tool therewith.

10 Claims, 4 Drawing Sheets

Related U.S. Application Data

(60) Provisional application No. 61/560,638, filed on Nov. 16, 2011.

(51) Int. Cl.
*A61M 39/22* (2006.01)
*A61B 17/00* (2006.01)

(52) U.S. Cl.
CPC .............. *A61B 2017/00477* (2013.01); *A61B 2017/347* (2013.01); *A61M 2025/0006* (2013.01)

(56) References Cited

U.S. PATENT DOCUMENTS

| | | | |
|---|---|---|---|
| 5,205,831 A | 4/1993 | Ryan | |
| 5,391,152 A | 2/1995 | Patterson | |
| 6,228,059 B1 | 5/2001 | Astarita | |
| 2002/0062106 A1* | 5/2002 | Chu | A61M 39/0613 604/167.01 |
| 2005/0171479 A1* | 8/2005 | Hruska | A61B 17/3498 604/167.06 |
| 2006/0264979 A1 | 11/2006 | Shepard | |
| 2008/0097386 A1 | 4/2008 | Osypka | |
| 2008/0262430 A1* | 10/2008 | Anderson | A61B 17/3415 604/164.1 |
| 2009/0306598 A1 | 12/2009 | Arcaro | |
| 2010/0004730 A1 | 1/2010 | Benjamin | |
| 2011/0092910 A1 | 4/2011 | Schultz | |
| 2012/0065590 A1* | 3/2012 | Bierman | A61M 25/0097 604/164.05 |

FOREIGN PATENT DOCUMENTS

| | | |
|---|---|---|
| JP | 2011-522589 | 8/2011 |
| JP | 2011-526815 | 10/2011 |
| WO | WO-2009148577 A1 | 12/2009 |
| WO | WO-2010002931 A1 | 12/2009 |

OTHER PUBLICATIONS

Parallel (n), American Heritage Dictionary, definition 3a and 3b, available Jul. 16, 2016, online at https://www.ahdictionary.com/word/search.html?q=parallel, 3 pages.

* cited by examiner

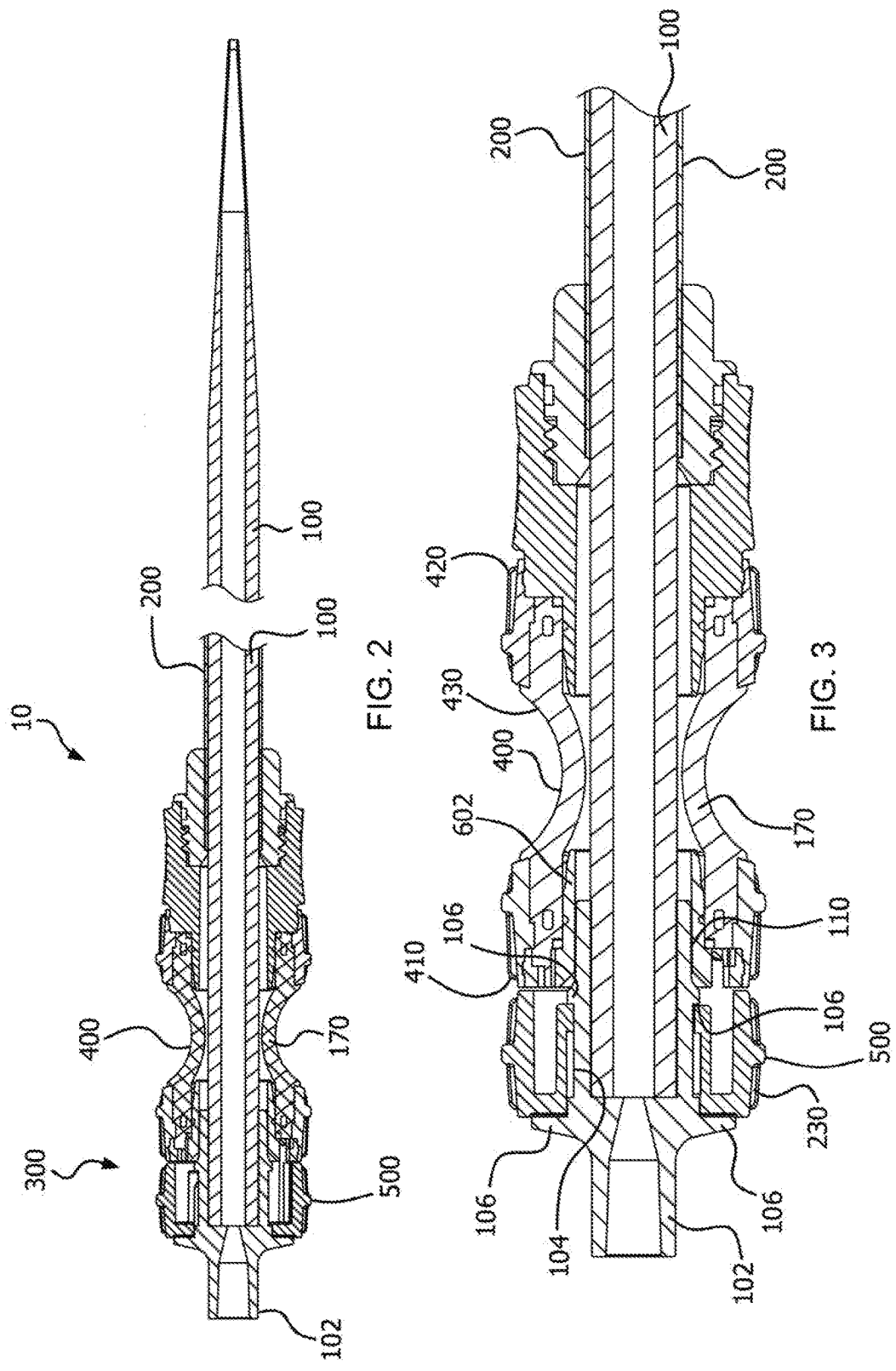

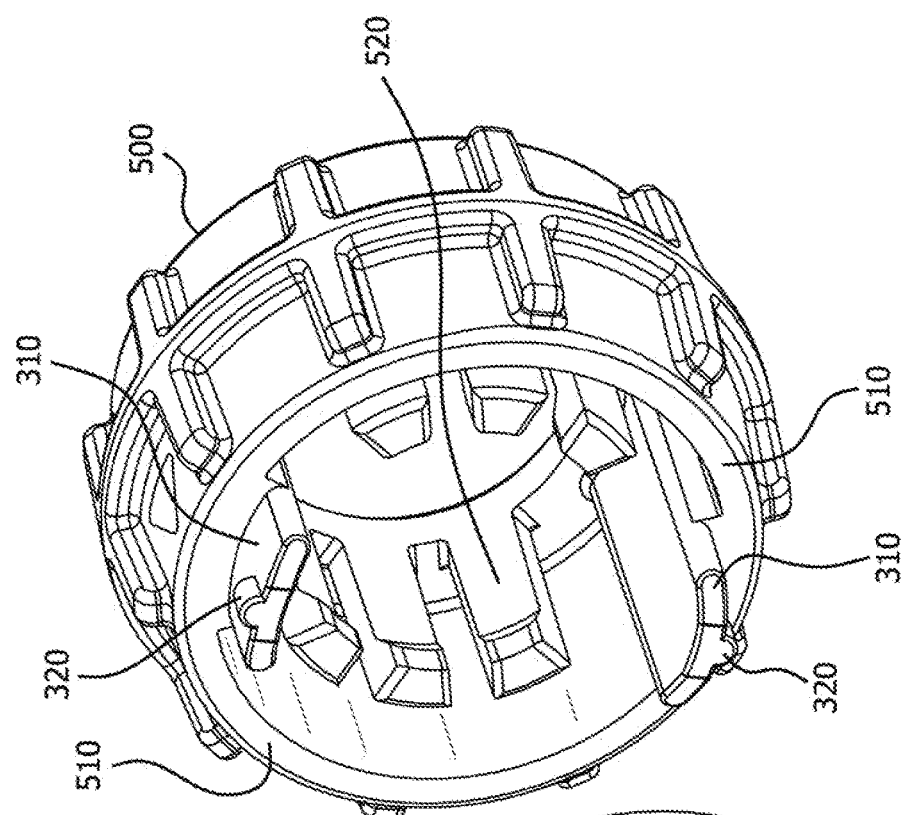
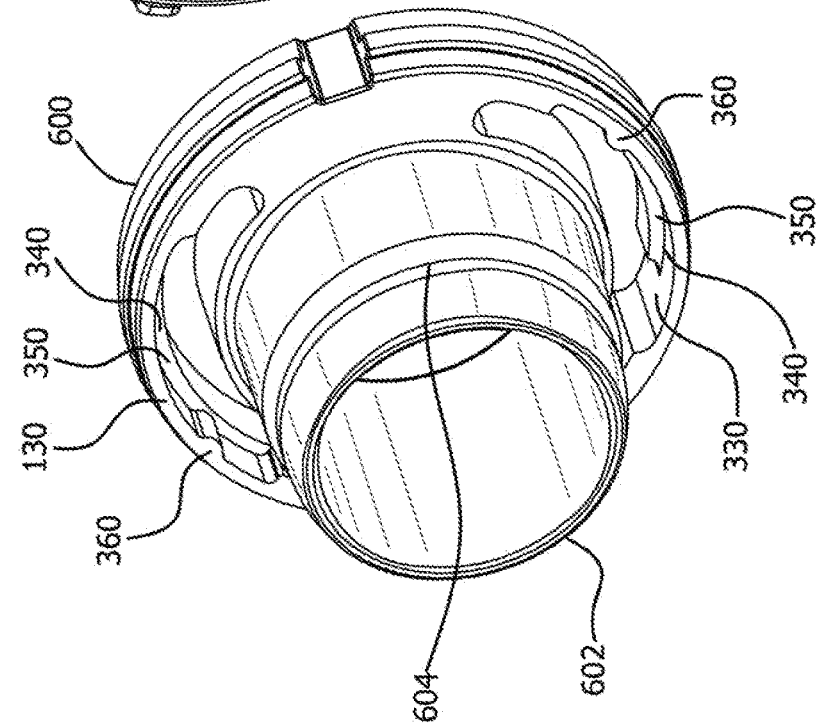
FIG. 4

INTRODUCER SHEATH ASSEMBLY HAVING A LOCKING DILATOR

CROSS-REFERENCE TO RELATED APPLICATIONS

This application is a Divisional of U.S. patent application Ser. No. 13/677,839, filed Nov. 15, 2012, which claims priority to U.S. Provisional Application 61/560,638 filed on Nov. 16, 2011, priority to both of those applications being claimed and the entire contents of both of those applications being incorporated herein by reference in their entireties.

BACKGROUND

Field

The invention relates to an introducer sheath assembly for medical procedures and, more particularly, a locking mechanism for releasably axially locking an introducer sheath and a surgical implement inserted through the introducer sheath.

Discussion

Introducer sheath assemblies are used in a wide variety of minimally invasive and conventional surgical procedures, such as endoluminal delivery of surgical implements. Introducer sheath assemblies typically include an introducer sheath and valve for controlling leakage while accessing the introducer sheath with surgical implements, such as endoprosthetic devices, dilators, guidewires and the like. Introducer sheath valves generally rely on contact between a resilient elastomeric sealing body and a surgical implement inserted through the introducer sheath valve to form a desired fluid tight seal. It remains desirable to provide a mechanism for locking an introducer sheath and surgical implement without disrupting the seal between the introducer sheath valve and surgical implement.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIG. 2 is a cross sectional view of an introducer sheath assembly in accordance with various embodiments;

FIG. 3 is an enlarged cross sectional view of an introducer sheath assembly in accordance with various embodiments;

FIG. 4 is an exploded perspective view of a locking mechanism in accordance with various embodiments;

DETAILED DESCRIPTION OF THE ILLUSTRATED EMBODIMENTS

An introducer sheath assembly, in accordance with various embodiments, is disclosed herein, which includes a locking mechanism for releasably axially locking the introducer sheath and a surgical implement or tool inserted through the introducer sheath assembly, such as dilators, endoprosthetics, endoscopes and the like. The introducer sheath assembly can include a sheath, and a valve for preventing leakage during insertion of a tool through the sheath. Examples and detailed descriptions of an introducer sheath assembly and valve are disclosed in co-pending U.S. Patent Application Publication 2009/0306598, the content of which is incorporated herein by reference in its entirety.

Figure 1:
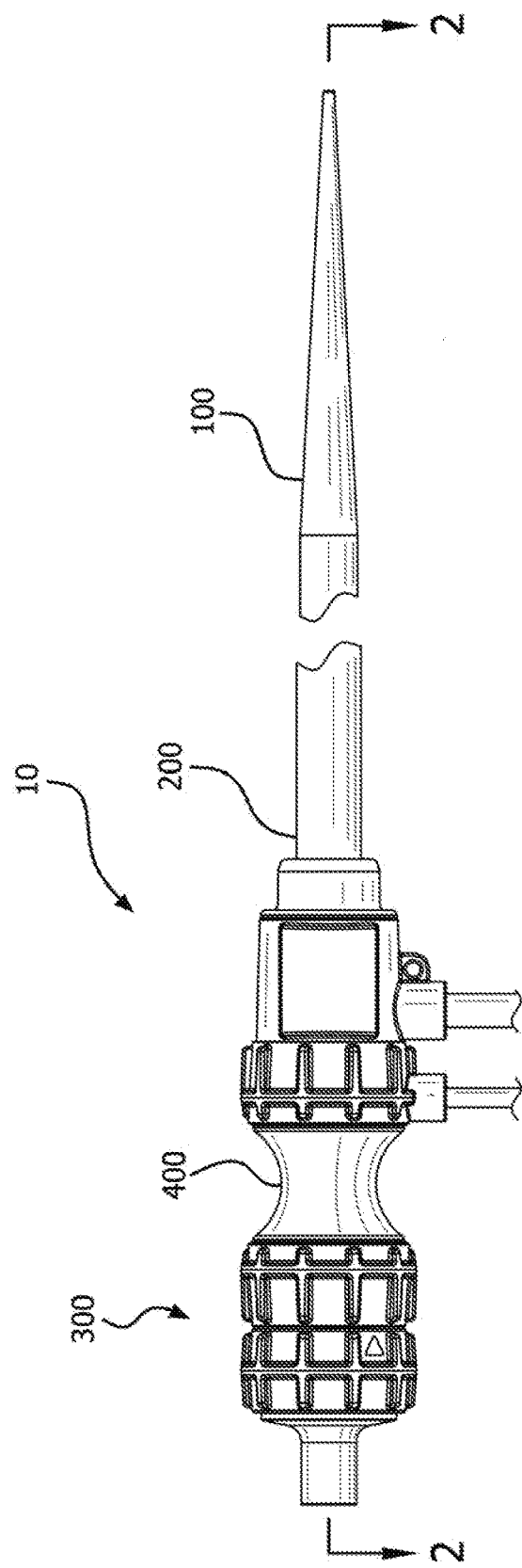
FIG. 1 is a side elevational view of an introducer sheath assembly in accordance with various embodiments.

Referring to FIG. 1, an introducer sheath assembly in accordance with various embodiments is shown and generally indicated at 10. The introducer sheath assembly 10 includes a tubular sheath 200 adapted to receive an elongated tool therethrough. In the figures, a tool 100 is shown illustratively as a dilator, though it should be readily appreciated that the tool can be any tool or device deliverable through the sheath, such as an endoscope or a stent graft. The introducer sheath assembly 10 can include a valve 400 to prevent leakage while inserting the tool 100 through the sheath 200. More specifically, the sheath 200 can be fixedly secured at one end 410 of the valve 400. The sheath 200 and a resilient inner tube 430 of the valve 400 can be generally coaxially aligned to receive the tool 100 therethrough. In various embodiments, described further in detail below, the introducer sheath assembly 10 includes a locking mechanism 300 that allows selective locking of the tool 100 to the sheath 200 and valve 400.

Referring to FIGS. 2 and 3, a locking mechanism 300 is disposed on an end 420 of the valve 400 opposite the sheath 200. The locking mechanism 300 is actuatable between locked and unlocked positions to allow selective locking of the tool 100 to the sheath 200 and valve 400. In various embodiments, the locking mechanism 300 includes a lock knob 500 rotatable between locked and unlocked positions to releasably axially lock the tool 100 to the sheath 200 or, more specifically, to the valve 400 without causing corresponding rotation of the tool 100 relative to the valve 400. In various embodiments, the tool 100 includes a hub 102. The hub 102 includes an annular bearing surface 104. The hub 102 includes radially outwardly extending locating surfaces 106 that are axially spaced apart on the bearing surface 104. The hub 102 also includes an annular portion 110 adjacent axially to the bearing surface 104. The annular portion 110 protrudes axially to facilitate alignment of the tool 100 as the tool 100 is inserted through the valve 400 and sheath 200. In other embodiments, the lock knob may be moveable in other directions, such as axially, relative to the hub The lock knob 500 includes at least one radially extending rib 520 that engages the annular bearing surface 104 of the hub 102, thereby generally radially locating the lock knob 500 relative to the hub 102. The rib 520 also axially engages the axially spaced apart locating surfaces 106, thereby axially locating and constraining the lock knob 500 relative to the hub 102. The lock knob 500 and hub 102 are, therefore, generally axially constrained relative to each other, but are also free to rotate relative to each other. Thus, as described below, the clinician can selectively rotate the lock knob 500 relative to the hub 102 to lock or unlock the locking mechanism 300 and not cause undesired rotation of the tool 100 relative to the sheath 200, valve 400 and/or vasculature.

The introducer sheath assembly 10 includes a trailing fitting 600 fixedly secured to the end 410 of the valve 400 opposite the sheath 200. More specifically, the trailing fitting includes an annular tapered portion 602. A resilient lip or ring (not shown) can be positioned along a slot 604 that extends around the annular portion 602. The ring can be formed from silicon or other suitable resilient sealing material. In assembly with the valve arrangement, the annular portion 602 of the trailing fitting 600 extends into the inner tube 430 of the valve 400. Insertion of the tapered portion 602 into the inner tube 430 during assembly causes the ring to engage and elastically radially displace or deform the inner tube 430 thereby forming a fluid seal therewith. The trailing fitting can also include a locking feature, such as a tab or barb extending through an aperture or recess, to secure its orientation relative to the valve once installed within.

The locking mechanism 300 includes a locking tab 310 extending generally axially from an end surface 510 of the lock knob 500. A protrusion 320 extends generally radially from an end of the locking tab 310 and is axially spaced apart from the end surface 510 of the lock knob 500. Alternatively, the locking mechanism 300 can include more than one locking tab. In FIG. 4, for example, a pair of locking tabs 310 extends from generally opposite sides of the end surface 510 of the lock knob 500.

Figure 5:
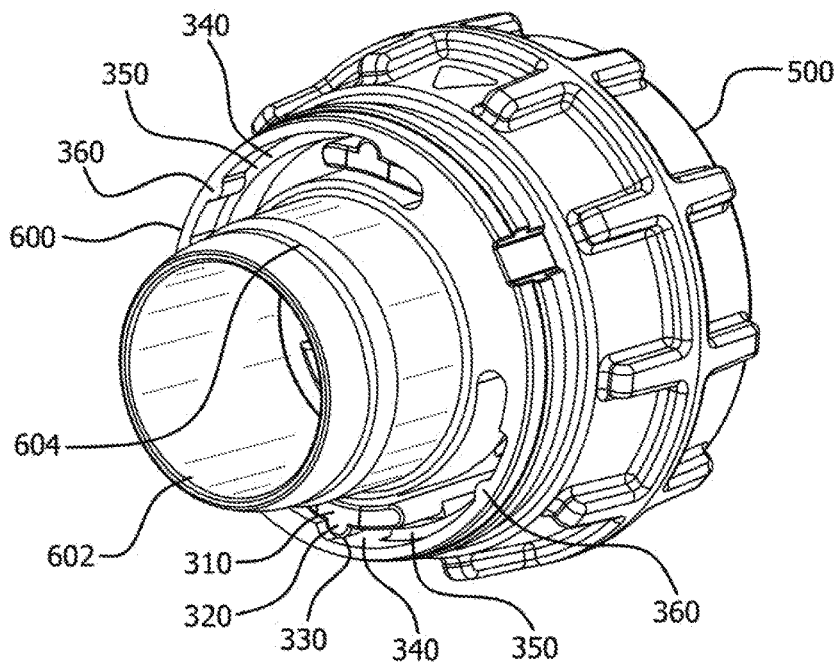
FIG. 5 is a perspective view of a locking mechanism in accordance with various embodiments shown in an unlocked position.
Figure 6:
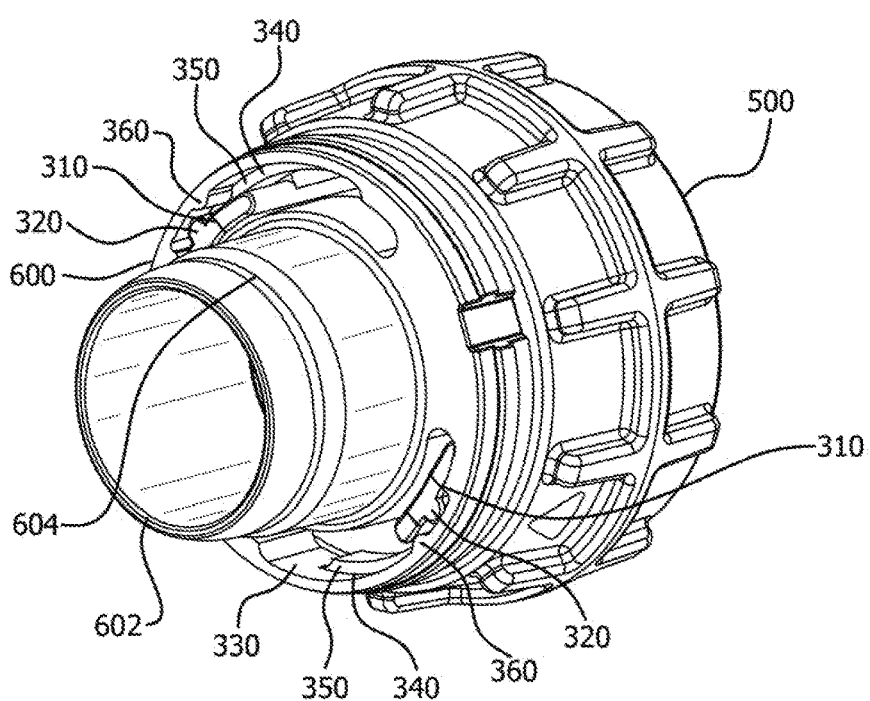
FIG. 6 is a perspective view of a locking mechanism in accordance with various embodiments shown in a locked position.

The locking mechanism 300 includes an axially extending groove 330 formed on the trailing fitting 600 to accommodate passing of each locking tab 310 therethrough as the lock knob 500 and trailing fitting 600 are positioned toward each other axially. The locking mechanism 300 includes an annular recess or slot 340 formed in the trailing fitting 600 that intersects with and extends rotationally from the groove 330 to accommodate the protrusion 320 as the lock knob 500 is rotated relative to the trailing fitting 600, for example, by an assembler during manufacture of the assembly or by a clinician when actuating the locking mechanism 300 to lock or release the tool 100 from the sheath 200 during an operating procedure. The locking mechanism 300 includes an annular edge 350 adjacent the annular slot 340 that axially can engage the protrusion 320 to axially interlock the lock knob 500 and the trailing fitting 600. The lock knob 500 is, therefore, selectively movable between an unlocked position (FIG. 5), wherein the protrusion 320 on the tab 310 of the lock knob 500 is aligned and movable along the axially extending groove 330 of the trailing fitting 600 to allow axial movement of the lock knob 500 relative to the trailing fitting 600, and a locked position (FIG. 6), wherein the protrusion 320 on the tab 310 of the lock knob 500 is aligned with and movable along the annular slot 340 such that the protrusion 320 can contact the annular edge 350 to axially interlock the lock knob 500 and the trailing fitting 600. As best shown in FIG. 6, a bump 360 formed on the trailing fitting 600 along the annular slot 340 can engage the protrusion 320 to hold the lock knob 500 rotatably toward the locked position.

An introducer assembly, in accordance with a number of embodiments, can utilize any tool or device deliverable through the sheath. Exemplary use of the introducer assembly is described below in connection with a dilator. It should, however, be readily appreciated that other surgical implements may be utilized with the introducer assembly, such as stent grafts, endoprosthetics, endoscopes, or other surgical implements. A guide wire is inserted endoluminally into a patient and toward an intended vascular treatment site. A flexible, elongated dilator is provided with a hub and lock knob for engaging the trailing fitting. The dilator is inserted through the valve and sheath. The annular portion of the hub radially aligns the dilator relative to the valve and sheath. The introducer sheath assembly, with the sheath, valve and dilator axially locked via the locking engagement of the lock and trailing fitting, as discussed above, is inserted into the patient along the guidewire. More specifically, the dilator is loaded onto the guidewire and inserted with the sheath into the patient along the guidewire. After dilating the intended endovascular delivery path, the dilator can be removed while the sheath remains in place. To remove the dilator, the lock is rotated so that the protrusion on the tab translates along the annular recess toward the axially extending groove until the protrusion is aligned with the groove. The protrusion translates through the groove as the lock and dilator are generally axially separated from the trailing fitting and valve arrangement.

As discussed, the lock knob freely rotates with respect to the hub and dilator. Thus, unlocking the lock knob from the trailing fitting does not cause undesired rotation of the dilator while still in the patient and further does not disturb fluid sealing engagement between the dilator and valve arrangement. Additionally, axial separation of the lock knob from the trailing fitting causes corresponding axial displacement of the dilator from the vasculature and sheath, as a result of the rib or ribs extending from the lock knob and engaging the locating surfaces of the hub. The dilator can be completely removed by continued axial separation of the lock knob relative to the trailing fitting. Thus, the locking mechanism allows selective locking and unlocking of the lock knob relative to the trailing fitting without causing rotation of the dilator and hub relative to the sheath and valve, while the tool remains in the vasculature of the patient and further without compromising fluid sealing engagement between the tool and the valve arrangement.

Although the valve arrangement has been discussed illustratively as an introducer sheath valve, various embodiments encompass other applications such as bariatric port access, medical injection port, vascular access port, valve for insertion sites such as feeding tubes or dialysis access port, etc.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of releasing an introducer sheath assembly having a longitudinal axis defining an axial direction along the longitudinal axis, a transverse direction transverse to the longitudinal axis, and a rotational direction about the longitudinal axis, the introducer sheath assembly including a valve, an introducer sheath secured at an end of the valve, an introducer tool coaxially received in the introducer sheath, and a fitting secured to the introducer sheath, the method comprising:

unlocking a locking mechanism of the introducer sheath assembly, including rotating a lock knob of the locking mechanism in the rotational direction to unlock the locking mechanism without causing movement of the introducer tool in the axial direction and without causing movement of the introducer tool in the rotational direction, wherein unlocking the lock knob does not disturb fluid sealing engagement between the introducer tool and the valve or cause rotation of the introducer tool relative to the introducer sheath during unlocking of the locking mechanism, and wherein unlocking the locking mechanism includes releasing the lock knob from the fitting by rotating the lock knob; and sliding the introducer tool from the introducer sheath in the axial direction after unlocking the locking mechanism, wherein the fitting includes an axially extending groove and wherein the lock knob includes an axially projecting lock tab and the fitting includes an annular slot receiving the lock tab to secure the lock knob to the fitting prior to unlocking the locking mechanism, and wherein the lock knob is configured to translate through the axially extending groove as the locking mechanism is axially separated from the fitting.

2. The method of claim 1, wherein the introducer sheath assembly includes the valve coupled to the introducer sheath, and further wherein unlocking the locking mechanism of the introducer sheath assembly includes unlocking the introducer tool from the valve.

3. The method of claim 2, wherein the valve sealingly engages the introducer tool, the method further comprising releasing the valve prior to sliding the introducer tool from the introducer sheath.

4. The method of claim 2, further comprising sealing the valve upon sliding the introducer tool from the introducer sheath.

5. The method of claim 1, wherein the introducer tool includes a hub and the lock knob of the locking mechanism is axially constrained by the hub during rotation of the lock knob.

6. The method of claim 5, wherein the hub defines an annular bearing surface that axially constrains the lock knob during rotation of the lock knob.

7. The method of claim 5, wherein the lock knob includes a radially extending rib that engages the hub that axially constrains the lock knob during rotation of the lock knob.

8. The method of claim 1, wherein the introducer sheath assembly includes the valve coupled to the introducer sheath, and further wherein locking the locking mechanism of the introducer sheath assembly includes locking the introducer tool to the valve.

9. A method of releasing an introducer sheath assembly having a longitudinal axis defining an axial direction along the longitudinal axis, a transverse direction transverse to the longitudinal axis, and a rotational direction about the longitudinal axis, the introducer sheath assembly including a valve, an introducer sheath secured at an end of the valve, an introducer tool coaxially received in the introducer sheath, and a fitting secured to the introducer sheath, the method comprising:

unlocking a locking mechanism of the introducer sheath assembly, including rotating a lock knob of the locking mechanism in the rotational direction to unlock the locking mechanism independent of rotation of the introducer tool or movement of the introducer tool in the axial direction, wherein unlocking the lock knob does not disturb fluid sealing engagement between the introducer tool and the valve or cause rotation of the introducer tool relative to the introducer sheath during unlocking of the locking mechanism, and wherein unlocking the locking mechanism includes releasing the lock knob from the fitting by rotating the lock knob; and sliding the introducer tool from the introducer sheath in the axial direction after unlocking the locking mechanism, wherein the fitting includes an axially extending groove and wherein the lock knob includes an axially projecting lock tab and the fitting includes an annular slot receiving the lock tab to secure the lock knob to the fitting prior to unlocking the locking mechanism, and wherein the lock knob is configured to translate through the axially extending groove as the locking mechanism is axially separated from the fitting.

10. A method of releasing an introducer sheath assembly having a longitudinal axis defining an axial direction along the longitudinal axis, a transverse direction transverse to the longitudinal axis, and a rotational direction about the longitudinal axis, the introducer sheath assembly including a valve, an introducer sheath secured at an end of the valve, an introducer tool coaxially received in the introducer sheath, and a fitting secured to the introducer sheath, the method comprising:

unlocking a locking mechanism of the introducer sheath assembly, including rotating a lock knob of the locking mechanism in the rotational direction to unlock the locking mechanism independent of rotation of the introducer tool or movement of the introducer tool in the axial direction, wherein unlocking the lock knob does not disturb fluid sealing engagement between the introducer tool and the valve or cause rotation of the introducer tool relative to the introducer sheath during unlocking of the locking mechanism; and sliding the introducer tool from the introducer sheath in the axial direction after unlocking the locking mechanism, wherein the lock knob includes an axially projecting lock tab and the fitting includes an annular slot receiving the lock tab to secure the lock knob to the fitting prior to unlocking the locking mechanism.

* * * * *